United States Patent [19]

Musser et al.

[11] Patent Number: 4,794,188

[45] Date of Patent: * Dec. 27, 1988

[54] CERTAIN UNSYMMETRICAL QUINOLINYL ETHERS HAVING ANTI-INFLAMMATORY AND ANTI-ALLERGIC ACTIVITY

[75] Inventors: John H. Musser, Malvern, Pa.; Utpal R. Chakraborty, Orangeburg, N.Y.

[73] Assignee: USV Pharmaceutical Corporation, Tuckahoe, N.Y.

[*] Notice: The portion of the term of this patent subsequent to Jan. 28, 2003 has been disclaimed.

[21] Appl. No.: 810,868

[22] Filed: Dec. 19, 1985

Related U.S. Application Data

[63] Continuation-in-part of Ser. No. 666,430, Oct. 30, 1984, abandoned, which is a continuation-in-part of Ser. No. 530,811, Sep. 9, 1983, Pat. No. 4,567,184, which is a continuation-in-part of Ser. No. 445,876, Dec. 1, 1982, abandoned.

[51] Int. Cl.$^4$ .................. C07D 215/22; C07D 217/24
[52] U.S. Cl. .................. 546/152; 546/122; 546/149; 546/153; 546/176; 546/180; 546/339; 546/344; 544/250; 544/283; 544/345; 544/353; 544/385; 544/408; 549/365
[58] Field of Search ................. 546/152, 149, 153, 180

[56] References Cited

U.S. PATENT DOCUMENTS

| 2,862,956 | 12/1958 | Gundel et al. | 560/73 |
|---|---|---|---|
| 4,360,700 | 11/1982 | Melvin, Jr. | 568/644 |

FOREIGN PATENT DOCUMENTS

| 0113587 | 7/1984 | European Pat. Off. | 546/344 |
|---|---|---|---|
| 2253511 | 7/1975 | France | 568/336 |
| 175293 | 12/1976 | New Zealand | 568/636 |
| 184606 | 6/1979 | New Zealand | 558/414 |
| 200031 | 11/1984 | New Zealand | 546/153 |

OTHER PUBLICATIONS

Boots, et al., Journal of Pharmaceutical Sciences, vol. 62, No. 6, Jun. 1973.
European Search Report, EP 83 11 2031.
Chemical Abstracts, vol. 94, 1981, p. 709, 174893.

Primary Examiner—Alan L. Rotman
Attorney, Agent, or Firm—Scully, Scott, Murphy & Presser

[57] ABSTRACT

Compounds of the formula:

$$Ar_1\text{-}X\text{-}Ar\text{-}Z\text{-}(R)_{n'}$$

and salts thereof, wherein $Ar_1$ is a nitrogen, sulfur or oxygen heterocyclic ring;

Ar is a phenyl ring or a nitrogen, oxygen or sulfur heterocyclic ring;

Ar and $Ar_1$ may be fully substituted or less than fully substituted with H, $CH_3$, lower alkyl, aryl, aralkyl, halo, hydroxy, lower alkoxy, $CF_3$, carboxy, alkylcarboxy, arylcarboxy, alkylcarbalkoxy, alkanoyl, formyl, oxo, nitrilo, amino, aminoalkyl, alkylamine, carboxamide, aryloxy, nitro, sulfonyl, sulfonamide, thio, alkylthio, hydroxyalkyl or oxyalkylcarbalkoxy;

X =

$$-O(CHR_1)_n-, \quad -S(CHR_1)_n-, \quad -NR_2(CHR_1)_n-\text{alkylene} \atop \underset{(O)_{n''}}{\|}$$

of up to 2 carbon atoms in the principal chain and up to a total of 4 carbon atoms, $$-C(R_1)=C(R_1)-, \quad -C\equiv C-, \quad -\underset{O}{\underset{\|}{C}}(CHR_1)_n-, \quad -\underset{OH}{\underset{|}{C}}H(CHR_1)_n-,$$

$$-CH=N-, \quad -\underset{O}{\underset{\|}{C}}-O-, \quad -\underset{O}{\underset{\|}{C}}-S-, \text{ or } -\underset{O}{\underset{\|}{C}}-N(R_1)-;$$

Z is an alkylene chain containing up to 10 carbon atoms in the principal chain and a total of up to 12 carbon atoms and from 0 to 2 double bonds and the said alkylene chain may be attached to Ar through an oxygen, sulfur or amino nitrogen atom, and when $n'=2$, one of the R substituents may be halogen on an omega carbon of the alkylene chain Z;

when $n'=1$, R is a substituent attached to one of the carbon atoms of Z selected from the group consisting of =O, $OR_3$, $SR_3$, $N(R_2)_2$ and $R_1$, $-COR_4$ and when $n'=2$ one R is previously defined and the additional R is a substituent attached to one of the carbon atoms of Z selected from the group consisting of =O, $OR_3$, $SR_3$, $N(R_2)_2$, $-COR_4$, lactone and halo;

$R_1$ is H or $CH_3$;

$R_2$ is H, lower alkyl, aryl or aralkyl;

$R_3$ is H, lower alkyl, lower alkanoyl, aryl, aralkyl or substituted aryl in which the substituent is halo, lower alkyl or lower alkoxy;

$R_4$ is $OR_2$ or $N(R_2)_2$;

n = 0 or 1;

n' = 1 to 7; and n'' = 0, 1 or 2.

36 Claims, No Drawings

CERTAIN UNSYMMETRICAL QUINOLINYL ETHERS HAVING ANTI-INFLAMMATORY AND ANTI-ALLERGIC ACTIVITY

DESCRIPTION OF THE INVENTION

This application is a continuation-in-part of application Ser. No. 666,430, filed Oct. 30, 1984, abondoned, which is a continuation-in-part of application Ser. No. 530,811, filed Sept. 9, 1983, now U.S. Pat. No. 4,567,184, which is a continuation-in-part of application Ser. No. 445,876, filed Dec. 1, 1982, abandoned.

This invention relates to new chemical compounds possessing valuable pharmaceutical activity. More particularly, the invention relates to novel lipoxygenase inhibitor compounds possessing anti-inflammatory and anti-allergic activities.

The present new compounds are of the formula:

  I and salts thereof,
wherein
$Ar_1$ is a nitrogen, sulfur or oxygen heterocyclic ring;
Ar is a phenyl ring or a nitrogen, oxygen or sulfur heterocyclic ring;
X =

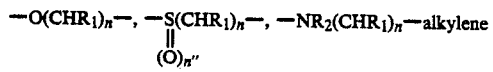

of up to 2 carbon atoms in the principal chain and up to a total of 4 carbon atoms,

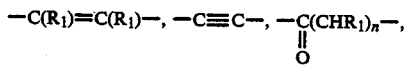

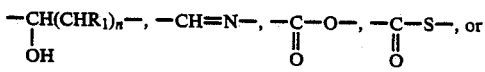

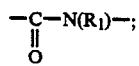

Z is an alkylene chain containing up to 10 carbon atoms in the principal chain and a total of up to 12 carbon atoms and from 0 to 2 double bonds and the said alkylene chain may be attached to Ar through an oxygen, sulfur or amino nitrogen atom, and when $n'=2$, one of the R substituents may be halogen on an omega carbon of the alkylene chain Z;
when $n'=1$, R is a substituent attached to one of the carbon atoms of Z selected from the group consisting of =O, $OR_3$, $SR_3$, $N(R_2)_2$, $-COR_4$ and $R_1$, and when $n'=2$, R is as previously defined and the additional R is a substituent attached to one of the carbon atoms of Z selected from the group consisting of =O, $OR_3$, $SR_3$, $N(R_2)_2$, $-COR_4$, lactone and halo;
$R_1$ is H or $CH_3$;
$R_2$ is H, lower alkyl, aryl or aralkyl;
$R_3$ is H, lower alkyl, lower alkanoyl, aryl, aralkyl or substituted aryl in which the substituent is halo, lower alkyl or lower alkoxy;
$R_4$ is $OR_2$ or $N(R_2)_2$;
$n=0$ or 1;
$n'=1$ to 7; and
$n''=0$, 1 or 2.

In the foregoing description, the lower alkyl and alkanoyl groups contain up to 6 carbon atoms which may be in the normal or branched configuration, including methyl, ethyl, propyl, isopropyl, butyl, isobutyl, amyl, isoamyl, hexyl, and the like. The aryl group is preferably phenyl, and aralkyl is benzyl. The alkanoyl group is preferably acetyl.

As employed herein, the expression "nitrogen, sulfur or oxygen heterocyclic ring" is meant to include those heterocyclic rings which include at least one sulfur, nitrogen or oxygen atom, but which may include one or several of the said atoms. This expression also is intended to include the so-called "benzo" heterocyclics. Representative heterocyclic rings include furan, thiophene, pyrrole, pyridine, pyrazine, thiazole, oxazole, quinoline, indole, benzothiophene, benzofuran, benzoxazole and the like, as well as N-oxides of the nitrogen heterocyclics.

Ar is preferably a monocyclic ring, e.g., phenyl, pyridine, thiophene, furan and pyrrole, while $Ar_1$ is preferably a bicyclic ring, e.g., quinoline, indole, benzofuran and benzothiophene. These rings are attached in their respective positions in the molecule of the present new compounds through any available carbon of the ring, but preferably through the 2-position of $Ar_1$.

Ar and $Ar_1$ may be fully substituted or less than fully substituted, e.g., mono- or di- or tri- or tetra-substituted with a variety of substituents such as H, $CH_3$, lower alkyl, aryl, aralkyl, halo, hydroxy, lower alkoxy, $CF_3$, carboxy, formyl, oxo, nitrilo, amino, aminoalkyl, alkylcarboxy, arylcarboxy, alkylcarbalkoxy, alkanoyl, alkylamine, carboxamide, aryloxy, nitro, sulfonyl, sulfonamide, thio, alkylthio, hydroxyalkyl or oxyalkylcarbalkoxy. It is preferred that the said substituents be present in intermediate compounds used in forming the final products as described in the disclosure of methods of preparation which follows. The substituents may be present on any of the available positions of the ring systems representative of Ar and $Ar_1$. Of course, substituents which are reactive under the synthetic conditions employed should be blocked using appropriate blocking groups which are readily removable after formation of the desired products. Such blocking groups are well known to those skilled in this art.

The preferred compounds are those in which $Ar_1$ is quinolyl, attached through any of the available positions. The preferred compounds are 2-quinolyl compounds.

The alkylene chains represented by Z can be normal or branched chains in which the branches are preferably methyl or ethyl and include those in which two such groups, e.g., methyl, are on the same carbon atom. The alkylene chains preferably contain up to 8 carbon atoms whether branched or normal. The alkylene chain may contain up to 2 double bonds and may be attached directly to the Ar ring through an oxygen, sulfur or amino nitrogen atom. In addition to substituent R, which is attached to one of the carbon atoms as depicted in the foregoing formula, other substituents such as halogen (F, Cl, Br or I) can be present on the alkylene chain, particularly on the terminal carbon.

Of the various groups representative of X in the foregoing formula, the preferred are those in which n=1, and especially those which include an oxygen function, particularly the group $-O(CHR_1)_n-$ in which n is 1 and $R_1$ is H. The disposition of the said groups between Ar and Ar₁ is not critical, e.g., the —O(CHR₁)$_n$—, can be attached with the oxygen directly on Ar₁ or on Ar. Preferably, the oxygen of —O(CHR₁) is attached to Ar₁.

In the most preferred compounds of this invention, Ar is phenyl, Ar₁ is 2-quinolyl, X is —OCH₂—, Z is alkylene of from about 5-8 carbon atoms and R is an oxygen-containing group, preferably, hydroxy, and n' is 1.

The present new compounds can be prepared by art-recognized procedures. For compounds in which X=—O(CHR₁)$_n$, any of the standard ether forming reactions can be employed as illustrated by the following general procedures:

(a) Ar₁(CHR₁)$_n$Y + HO—AR—Z—(R)$_{n'}$ (b) Ar₁(CHR₁)$_n$OH + Y—Ar—Z—(R)$_{n'}$ (c) Ar₁Y + HO(CHR₁)$_n$—Ar—Z—(R)$_{n'}$

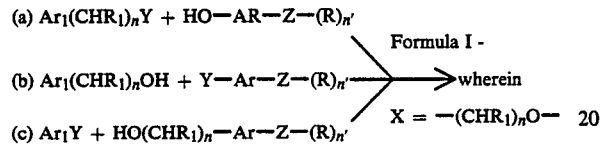

In these modifications, Y is a leaving group, most commonly halogen, preferably Cl, Br or I, which forms HY with the hydrogen of the alcohol. Illustrative of processes (a) and (b), 2-chloromethylquinoline is condensed with 1-(3-hydroxyphenyl)-1-pentanol and 2-hydroxymethylquinoline is condensed with 1-(3-bromophenyl)-1-pentanol to form the same product. Illustrative of process (c) is the condensation of 2-bromopyridine with 5-(1-hydroxyhexyl) furfuryl alcohol to form the corresponding pyridyl-furylmethyl ether. Alternatively, the leaving group can be a sulfonate ester group, such as the tolyl sulfonate group, which forms toluenesulfonic acid with the hydrogen of the OH group. In all cases where an acid is the by-product, it is preferred to use an acid acceptor to neutralize the acid in the reaction mixture. Such acid acceptors are well-known in the art and include various alkali and alkaline earth metal carbonates and bicarbonates, e.g., sodium carbonate, potassium bicarbonate, cesium carbonate and like, alkali metal alkoxides such as sodium ethoxide, potassium ethoxide and the like, as well as organic amines such as pyridine, pyrrole, dimethylamine, and similar such amines. Of course, when Ar₁ and/or Ar includes a basic nitrogen heteroatom, this can serve as the acid acceptor and the product is obtained as an acid salt.

To form compounds in which X is

the same reactions can be used employing the corresponding mercaptans in lieu of the alcohols. The sulfoxides and sulfones (where n''=1 or 2) can be formed by the known reaction with peroxides such as hydrogen peroxide or benzoylperoxides.

For compounds in which X is —NR₂—(CHR₁)$_n$—, the corresponding amino starting compounds are employed to form the desired amino coppound. Thus, 2-aminopyridine is condensed with 3-(1-hydroxyhexyl)-benzyloromide to form 2-[3-(1-hydroxyhexyl)benzylamino]pyridine. Alternatively, 2-quinolylmethylbromide is condensed with 3-(1-hydroxyhexyl)aniline to form 2-[3-(1-hydoxyhexyl) anilinomethyl]quinoline.

Compounds in which X is —CH═N— are so-called anils and are prepared by condensing an aldehyde with the corresponding amine. Thus, 2-aminopyridine can be condensed with 5-(1-hydroxybutyl)furfural to form the corresponding anil. Alternatively, thiophene-2-aldehyde can be condensed with 5-(1-hydroxypentyl) pyrrolylmethylamine to form the corresponding anil.

For those compounds in which X is

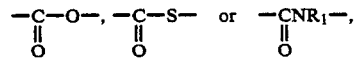

the acid Ar₁COOH is esterified with HO—Ar—Z(R)$_{n'}$, or the corresponding mercaptans, and the amide is formed by reaction of a suitable derivative of the acid with the amine, HNR₁Ar—Z(R)$_{n'}$. Since the group —Z(R)$_{n'}$ may contain a group reactive with the aforesaid acid derivatives, it is preferred that the desired group —Z(R)$_{n'}$ be formed after the acylation reaction is completed. This can be accomplished by providing a group convertible to the desired group in the Ar nucleus. Such convertible groups include, for example, the nitrilo and formyl groups, which after acylation, can be converted to aminoalkyl in the case of the nitrilo group or to hydroxyalkyl in the case of the formyl group, e.g., by reaction with a Grignard reagent to form a secondary alcohol of any desired carbon length. The position of the amino or alcohol hydroxy groups can be set by merely selecting the length of carbon chain (where present) separating the nitrilo or formyl group from the Ar ring carbon as should be obvious to those skilled in the art.

Of course, the group —Z(R)$_{n'}$ may contain groups which are non-reactive in formation of the X-linkage between Ar and Ar₁ and such groups as are non-reactive may be present on the Ar nucleus before such formation, e.g., ether groups such as alkoxy, alkymercapto, phenoxy, and the like, keto-carbonyl, alkoxy-carbonyl and carboxamido groups. After formation of the X-linkage, such non-reactive groups can be converted to 1°, 2° or 3° alcohol groups by reduction of a carbonyl or reaction with a Grignard reagent with the carbonyl or by reduction of an ester group, COOR₄.

For compounds in which Z is ethylenic, Ar₁CH₂Y is condensed with

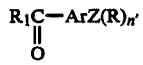

to form the desired ethylenic compound. From those in which R₁ is H, the corresponding acetylenic compounds can be obtained by halogenation to form the dihalo compound and dehydrohalogenation to remove 2 equivalents of hydrogen halide.

Many obvious variations of the foregoing procedures will be apparent to those skilled in the art for preparing compounds of the invention.

The compounds of the invention containing basic nitrogen form salts with acids, both organic and inorganic acids. Of particular value are salts with pharmaceutically-acceptable acids especially in dosage forms predicated on aqueous systems where the enhanced water solubility of the salts is most advantageous. Salts formed with pharmceutically unacceptable acids are also useful in the isolation and purification of the basic nitrogen-containing present new compounds. Salts include those formed with hydrochloric, sulfuric, nitric, perchloric, benzenesulfonic, toluenesulfonic, phosphoric, acetic, malic, malonic, tartaric and similar such acids.

The compounds of the invention also exist in stereoisomeric forms due to the presence of asymmetric centers in the molecule, especially in the group $-Z(R)_{n'}$ and in the linkage $-X-$ (where $R_1$ is other than H) or in other parts of the molecule. This invention contemplates the stereoisomers individually or in mixtures or as the racemic compound. The individual stereoisomers can be obtained by standard resolution procedures known to those skilled in the art or by stereospecific synthesis.

The compounds of the present invention can be administered to the host in a variety of forms adapted to the chosen route of aministration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeuticalyy useful compositions is such that a suitable dosage will be obtained. Preferred compositions or preparations according to the present invention are prepared so that an oral dosage unit fcrm contains between about 50 and 300 mg of active compuund.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or aaccharin may be added or a flavoring agent such as peppermint, oil of wintergreen, or cherry flavoring. When the doagc unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for examplc, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present thereapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 $\mu$M/day or from about 0.1 mg to about 50 mg/kg of body weight per day and higher although it may be administered in several different dosage units. Higher dosages are required for oral administration.

The following examples are illustrative.

EXAMPLE 1

A. 1-(3-hydroxyohenyl)-1-pentanol

A dried 1 L 3-neck flask equipped with a $N_2$ inlet, reflux condenser, mechanical stirrer and a 500 ml drppping funnel was charged with 24.3 g (1.0 mol) of magnesium and 50 ml of anhydrous ether. To this was added 15 g (0.11 mol) of 1-bromobutane (Aldrich 23,988-7) and one crystal of iodine. The dropping funnel was charged with 122 g (0.89 mol) of 1-bromobutane and 100 ml. of anhydrous ether. After the contents of the reaction flask began to reflux, the flask was cooled with a water/ice bath and the 1-bromobutane solution was added at such a rate as to maintain a gentle reflux. After the addition was complete the reaction mixture was refluxed for one-half hour, then cooled to 0° C. in an ice/water bath. The dropping funnel was then charged with 38.0 g (0.311 mol) of 3-hydroxybenzaldehyde (Aldrich H 1,980-8) and 250 ml of anhydrous ether. This slurry was added over a 1 hour period. After the addition the reaction mixture was allowed to warm up to room temperature and was stirred overnight. The reaction mixture was neutralized with 900 ml of 5% aqueous HCl. The reaction mixture was extracted with 2×500 ml of ethyl acetate, the organic extracts combined, washed with 1L of water, dried over anhydrous sodium sulfate and concentrated under reduced pressure. The crude product was recrystallized from ethyl acetate to yield 44.0 g (79%) of 1-(3-hydroxyphenyl)-1-pentanol, m.p. 120°-122° C.

In like manner as above, using appropriate starting materials and reagents, the following compounds were prepared:
1-(3-hydroxyphenyl)-1-hexanol;
1-(3-hydroxyphenyl)-1-methyl-1-pentanol (using 3-hydroxyphenyl methyl ketone in lieu of the aldehyde); and
1-(2-hydroxyphenyl)-1-hexanol.

B. 1-[3-(2-benzofurylmethoxy)phenyl]-1-hexanol

2-Bromomethylbenzofuran (5 g, 0.024 mol) and 1-(3-hydroxyphenyl)-1-hexanol (4.7 g, 0.024 mol) were dissolved in DMSO (75 ml). To this clear, homogeneous solution was added an aqueous solution of sodium hydroxide (12.5 ml, 2N solution; 0.025 mol NaOH). Immediately after the sodium hydroxide solution was added, the reaction mixture became warm (45°-50° C.). This clear, homogeneous solution was stirred at room temperature for 6 hours, and then poured into water (300 ml). The organics were extracted thoroughly with ethyl acetate (3×50 ml), and the combined organic extract was washed with water, 1N sodium hydroxide solution (to remove excess phenol), water, 0.1N hydrochloric acid solution, water and finally brine. After drying over anhydrous magnesium sulfate, all volatiles were removed from the ethyl acetate extract to leave a clear liquid (7.2 g) which was chromatographed on silica gel using 10% ethyl acetate in hexanes as eluent to obtain the pure compound as a clear, colorless liquid (4.4 g, 56%).

In like manner as above, using appropriate starting materials and reagents, the following compounds are prepared:
2-[3-(1-hydroxyhexyl)phenoxymethyl]quinoline;
2-[3-(1-hydroxyhexyl)phenoxymethyl-5-methylfuran;
2-[3-(1-hydroxyhexyl)phenoxymethyl]indole;
2-[2-(1-hydroxyhexyl)phenoxymethyl]oxazole;
2-[3-(1-hydroxyhexyl)phenoxymethyl]furan;
2-[3-(1-hydroxyhexyl)phenoxymethyl]thiazole;
2-[4-(1-hydroxyhexyl)phenoxymethyl]pyridine;
2-[3-(1-hydroxyhexyl)phenoxymethyl]benzoxazole;
6-[3-(1-hydroxyhexyl)phenoxymethyl]picolinyl nitrile;
2-[3-(1-hydroxyhexyl)phenoxymethyl]thiophene; and
2-[3-(1-methyl-1-hydroxypentyl)phenoxymethylquinoline hydoochloride.

EXAMPLE 2

2-[4-(1-hydroxyhexyl)phenoxymethyl]pyrrole

A mixture of 2-chloromethyl pyrrole (5.8 g, 0.05 mol), 1-(4-hydroxyphenyl)-1-hexanol (9.75 g, 0.05 mol), finely powdered anhydrous potassium carbonate (7 g, 0.05 mol) and sodium iodide (0.75 g, 0.005 mol) in anhydrous acetone (125 ml) were refluxed for 6 hours. The reaction mixture was filtered, and the residue was washed with acetone (25 ml). The filtrate was concentrated at the rotary evaporator to about 25–30 ml and the dark liquid was taken up in ethyl acetate (100 ml). The organic extract was washed with 5% sodium hydroxide solution, water and brine, and then dried over $MgSO_4$. All volatiles were removed, and the dark oil was chromatographed on silica gel (15% ethyl acetate in hexanes) to leave the desired product as a light yellow liquid (4.1 g, 30%).

Using this procedure, 6-[3-(1-hydroxyhexyl)phenoxymethyl]picolinic acid (m.p. 111°-113° C.) was prepared.

EXAMPLE 3

2-[5-(1-Hydroxyhexyl)-2-pyridyloxymethyl]indole

2-Chloromethyl indole (8 g, 0,048 mol) and 2-hydroxy-5-(1-hydroxyhexyl)pyridine (9.36 g, 0.048 mol) were dissolved in DMSO (250 ml) and to this mixture, 2N sodium hydroxide solution was added (25 ml, 0.05 mol). The clear, homogeneous reaction mixture became warm, and this mixture was stirred at room temperature overnight. The solution was poured into warer (500 ml), and was extracted thoroughly with ethyl acetate (4×50 ml). The combined extract was washed with 1N sodium hydroxide sclution, water and brine. After drying the organic extract over $MgSO_4$, all volatiles were removed to leave a brown oil (9 g). This crude product was purified by HPLC (silica gel, 20% ethyl acetate in hexane) to yield the pure product (8.6 g, 55%) as a yellowish semi-solid.

EXAMPLE 4

2-[5-(1-Hydroxyhexyl)-2-furylmethoxy]pyridine

To a suspension of sodium hydride (2.5 g, 0.104 mol) in dry DMF (100 ml) containing 2-chloropyridine (11.35 g, 0.10 mol), a solution of 5-hydroyymethyl furfural (12.6 g, 0.10 mol) in dry DMF (75 ml) was added dropwise. The reaction mixture was stirred vigorously with a mechanical stirrer. After the addition was complete (90 min.), the solution was slowly heated to about 80°-90° C. for 12 hours. The slightly turbid reaction mixture was cooled to room temperature,aand then most of the volatiles were removed. The residue was taken up in ethyl acetate, and was washed with water and brine. The ethyl acetate extract was dried over anhydrous magnesium sulfate, and then all volatiles were removed to leave the crude aldehyde intermediate (16 g, 79% yield). This product on NMR and mass spectroscopic investigation was found to be pure enough to be used for the next step.

The crude intermediate aldehyde (6.1 g, 0.03 mol) was dissolved in dry THF (50 ml), and cooled to −15° to −20° C. (dry ice-brine). To this cold solution of the aldehyde was added slowly, a solution of n-pentyl magnesium bromide (prepared from 4.55 g (0.03 mol) of 1-bromopentane and magnesium turnings (0.73 g, 0.03 mol) in THF (35 ml)). After the addition was complete (30 min.), the reaction mixture was stirred at this temperature for another hour, and finally allowed to warm up to room temperature. The reaction mixture was then quenched carefully by adding cold methanol, followed by a 5% ammonium chloride solution. Most of the THF was then removed at the rotary evaporator, and the residue was dissolved in ethyl acetate. The organic extract was washed with water and brine, and then dried over MgSO$_4$. The crude product (6.75 g) obtained after removal of all solvent was purified by chromatography on silica gel (18% ethyl acetate in hexane) to give 5.03 g (61%) of the pure product.

EXAMPLE 5

4-[2-(1-Hydroxyhexyl)-5-thienylmethoxy]quinoline

To a well-stirred solution of 4-hydroxyquinoline (2 g, 0.014 mol) and 5-bromomethyl-2-(1-hydroxyhexyl)thiophene (3.82 g, 0.014 mol) in DMSO (50 ml) was added a 2N solution of sodium hydroxide (8 ml, 0.016 mol). The mixture became warm immediately. This clear solution was stirred overnight at room temperature, and then was poured into water (200 ml). The aqueous solution was extracted thoroughly with ethyl acetate (4×30 ml). The organic extract was washed with water and brine, and then dried over MgSO$_4$. All volatiles were removed, and the crude product was purified chromatographically (silica gel; 15% ethyl acetate in hexane) to yield 2.1 g (44%) of the pure product.

EXAMPLE 6

2-[2-(1-Hydroxyhexyl)-5-pyridyloxy]quinoline

To a suspension of sodium hydride (3.6 g, 0.15 mol) in dry DMF (150 ml) containing 2-chloroquinoline (24.5 g, 0.15 mol) was added dropwise a solution of 5-hydroxypyridine-2-carboxaldehyde (18.5 g, 0.15 mol) in dry DMF (75 ml). The solution was stirred vigorously with a mechanical stirrer. After the addition was complete (90 min.), the reaction was heated to about 90° C. for 12 hours. Most of the DMF was removed, and the residue was carefully poured into cold water. The aqueous solution was extracted with ethyl acetate (4×30 ml), and the organic extract was washed with water, brine, and then dried over MgSO$_4$. All volatiles were removed to leave the crude aldehyde intermediate (26 g) which was pure enough to be used in the next step.

To a cold (−30° C.) solution of 5-(2-quinolinyloxy)-2-pyridine carboxaldehyde (8 g, 0.032 mol) in dry THF (125 ml) was added a solution of pentylmagnesium bromide (prepared from 4.83 g (0.032 mol) of 1-bromopentane and 0.78 g (0.032 mol) of Mg turnings in THF (60 ml). After the addition of the Grignard reagent was complete (−45° C.), the solution was stirred at this temperature for 90 minutes, and allowed to slowly warm up to room temperature in about 2 hours. The reaction was quenched by adding a saturated solution of ammonium chloride. The clear organic layer was decanted, and most of the volatiles were removed. The residue was taken up in ethyl acetate, and then washed with water, brine, and dried over MgSO$_4$. After removal of the ethyl acetate the crude residue (7.7 g) was purified by HPLC (silica gel; 25% ethyl acetate in hexane) to give 3.6 g (35%) of pure product.

EXAMPLE 7

2-[3-(1-Hydroxy-2-methylhexyl)phenoxymethyl]quinoline

A. A solution of the ketone, 2-(3-hexanoylphenoxymethyl)quinoline (prepared from 3-hexanoylphenol and 2-chloromethyl quinoline)(6 g, 0.018 mol) in dry THF (25 ml) was added slowly to a mildly refluxing suspension of sodium hydride (1.3 g, 0.054 mol) in dry THF (75 ml) containing excess methyl iodide (10.3 g, 0.073 mol) After the addition of the ketone was complete (30 min.), the reaction mixture was refluxed for 4 hours. After cooling the mixture to room temperature, excess NaH was destroyed by adding methanol. All volatiles were removed at the rotary evaporator and the residue was taken up in ethyl acetate. The organic extract was washed with water and brine, and dried over anhydrous magnesium sulfate. Upon removal of all solvent, the mono-methylated eetone (2-[3-(2-methylhexanoyl) phenoxymethyl]quinoline, was obtained as a yellow oil weighing 8 g.

B. This ketone (8 g) was next reduced with sodium borohydride (1.4 g, 0.036 mol) in ethanol (100 ml) at room temperature for about 15 hours. A little water and methanol was added to the reaction mixture, and then most of the volatiles were removed at the rotary evaporator. The residue was thoroughly extracted with ethyl acetate, and the organics were washed with water, brine, and then dried over anhydrous MgSO$_4$. All solvent was removed to leave a yellow oil (6 g) which was chromatographed on silica gel using 20% ethyl acetate in hexane as eluent. The desired mono methylated alcohol was obtained as a yellowish solid (1.5 g), mp. 64°–67° C.

EXAMPLE 8

2-[3-(1-Hydroxy-2,2-dimethylhexyl)phenoxymethyl]-quinoline

A. The ketone 2-(3-(2,2-dimethylhexanoyl)phenoxymethyl)quinoline (4 g) was treated with sodium borohydride (0.9 g) in ethanol (70 ml) at room temperature for about 15 hours. The solution was cooled in an ice bath, and excess of borohydride was destroyed by adding cold, dil HCl solution dropwise. After all the reducing agent was destroyed, the pH of the solution was adjusted to about 5–6, and then most of the volatiles were removed. The residue was taken up in ethyl acetate, and the organics were washed with water, brine and dried over MgSO$_4$. The crude alcohol was isolated by removing all solvents. The pure alcohol (1.6 g, 114°–116° C.,), was isolated by chromatography on silica gel using 20% ethyl acetate in hexane as eluent.

B. Preparation of 2-(3-(2,2-dimethylhexanoyl)-phenoxymethyl quinoline (starting compound for A. procedure):

A mixture of 2-chloromethylquinoline (12.1 g), 3-(2,2-dimethylhexanoyl)phenol (15 g), finely powdered anhydrous potassium carbonate (20 g) and potassium iodide (0.05 g) in dry acetone (300 ml) was refluxed overnight. The suspension was filtered, and most of the volatiles were removed at the rotary evaporator. The residue was taken up in ethyl acetate, washed with 5% NaOH solution, water, brine, and the extract was dried.

On removal of all solvent, the crude ether was obtained as a yellow oil. This oil was purified on HPLC (Prep. 500, Waters) using 10% ethyl acetate in hexane as eluent. The pure material was isolated in about 48% yield (12 g) as a light yellow oil.

C. Synthesis of 3-(2,2-dimethyl hexanoyl)phenol

The benzyl ether of the desired phenol (26 g) was taken in methanol (150 ml) and this solution was hydrogenated in a Parr apparatus under an atmosphere of hydrogen (45–50 lbs./sq.in.) in the presence of 10% palladium on charcoal (10 g). After 20–24 hours, the suspension was filtered on celite; all methanol was removed to obtain the desired phenol in about 83% yield (15.4 g) as a coloress liquid.

The benzyl ether starting compound was prepared by oxidation of 3-(1-hydroxyhexyl)phenyl benzyl ether to the corresponding ketone followed by alkylation with methyl iodide to form the 2,2-dimethyl compound.

In similar manner, using appropriate starting materials and reagents, the following compounds and the corresponding ketones are prepared:

2-[3-(1-hydroxy-2-isobutylhexyl)phenoxymethyl]benzofuran;

2-[3-(1-hydroxy-2,2-diethylpentyl)phenoxymethyl]thiophene; and

2-[3-1-hydroxy-2-methylhexyl)phenoxymethyl]benzothiophene.

EXAMPLE 9

2-[3-(1-Hydroxyhexyl)phenoxy]methyl]pyridine hydrochloride

A suspension of 3.3 g of picolyl chloride hydrochloride (Aldrich 16,270-1), 1-(3-hydroxyphenyl)-1-hexanol (3.9 g), cesium carbonate (16.3 g), cesium iodide (trace) and acetone were refluxed for 40 hours. The reaction was filtered through a pad of celite and silica gel and the solvent removed in vacuo. The remaining oil was dissolved in ethyl ether, filtered through celite and silica gel and treated with ethereal hydrochloric acid. The resulting white precipitate was filtered, washed (ethyl ether) and dried giving 4.2 g (66% yield) of solid, m.p. 164°–165° C.

In like manner as above using appropriate starting materials and reagents, the following compounds were prepared:

3-[[3-(1-Hydroxyhexyl)phenoxy]methyl]pyridine hydrochloride, m.p. 162°–163° C.;

2-[[3-(1-Hydroxyhexyl)phenoxy]methyl]quinoline hydrochloride, m.p. 90°–95° C.; and 4-[[3-(1-Hydroxyhexyl)phenoxy]methyl]pyridine hydrochloride, m.p. 160°–160.5° C.

EXAMPLE 10

Methyl 6-[[3-(1-hydroxyhexyl)phenoxy]methyl]picolinate

A solution of 6-[[3-(1-hydroxyhexyl)phenoxy]methyl]picolinyl nitrile (1.1 g), methanol (50 ml) and cesium carbonate was stirred at room temperature overnight. The reaction mixture was diluted with 0.1N hydrochloric acid. After stirring for three hours, the methanol was removed in vacuo and the remaining suspension was extracted with chloroform. The organic extract was dried (MgSO4) and concentrated to an oil (7.6 g, 94% yield).

In like manner as above, using appropriate starting materials and reagents, the following compounds were prepared:

Ethyl 2-(3-(2-quinolinylmethoxy)phenoxy)propionic acid;

Ethyl 2-(3-(2-quinolinylmethoxy)phenyl)propionic acid.

EXAMPLE 11

2-(3-Hexanoylphenoxymethyl)quinoline

A solution of 1-(3-hydroxyphenyl)-1-hexanol (3 g) in methylene chloride (200 ml) was added to a well-stirred suspension of pyridinium chlorochromate (5.1 g) and sodium acetate (2.5 g) in methylenechloride (150 ml). The mixture was stirred at room temperature for two hours. Ether (100 ml) was added, and the brown granular preiipitate was removed by filtration. All volatiles were removed from the filtrate, and the residual liquid was purified by chromtography on silica gel using ether as eluent. The desired ketone, 3-hexanoylphenol, was isolated as a clear, colorless oil.

This ketone (1.2 g) was refluxed with 2-chloromethylquinoline hydrochloride (1.3 g), potassium carbonate (8.6 g), potassium iodide (0.05 g) and cesium carbonate (0.05 g) in acetone (300 ml) for 24 hours. The reaction mixture was filtered, and the filtrate was concentrated, dissolved in chloroform, and then washed with sodium hydroxide solution (5%), water and brine. After drying this solution over MgSO4, all volatiles were removed. The residue was purified by chromatography on silica gel (25% ethyl acetate in hexanes). The pure desired product was isolated as a tan solid, m.p. 52°–55° C.

EXAMPLE 12

2-(3-(2-(2-Hydroxy)heptyl)phenoxymethyl)quinoline hydrochloride

A mixture of 2-chloromethyl quinoline hydrochloride (3.1 g) and 2-(3-hydroxyphenyl)-2-heptanol (3 g) in acetone (300 ml) containing potassium carbonate (20 g) and potassium iodide (0.2 g) was refluxed overnight. The reaction mixture was cooled, and most of the volatiles were removed at the rotary evaporator. The residue was taken up in ethyl acetate, and was washed with sodium hydroxide solution (5%) and brine. The organic layer was dried over magnesium sulfate and all solvent was removed to leave the crude product (weighing about 6 g), which was purified by chromatography (silica gel; 20% ethyl acetate in hexanes). The free base, isolated as an oil, was dissolved in dry ether, and treated with hydrogen chloride gas to give the pure desired salt as a white solid, m.p. 125° C. (dec.).

In like manner as described above, using appropriate starting materials and reagents, 2-(3-(2-(2-hydroxy)heptyl)phenoxymethyl)pyridine hydrochloride, m.p. 160°–665° C., was prepared.

EXAMPLE 13

2-[3-(1-Hexenyl)phenoxymethyl]quinoline

Sodium ethoxide was prepared by dissolving sodium metal (0.9 g) in absolute ethanol (50 ml). 3-Hydroxybenzaldehyde (5 g) in alcohol (50 ml) was added to sodium ethoxide and the mixture was refluxed for one hour. The reaction mixture was cooled, and a solution of 2-chloromethyl quinoline (7.3 g) in alcohol (50 ml) was added. The mixture was refluxed for one day. All volatiles were removed, and the residue was taken up in ethyl acetate. The organic extract was washed with aqueous sodium hydroxide (5%) solution, water and brine. After drying, all solvent was removed. The residual oil was chromatographed on silica gel using 15% ethyl acetate in hexane as eluent and the pure aldehyde was isolated.

N-pentyl-triphenylphosphonium bromide (3.1 g), prepared by refluxing a toluene solution of 1-bromopentane and triphenylphosphine, and filtering the white phosphonium salt, was dissolved in tetrahydrofuran (100 ml.) The solution was cooled to 0° C., and n-butyl lithium (7.6 mmol; 2.3M solution in hexane) was added. The mixture was stirred at room temperature for one hour, then cooled again to 0° C., and a solution of the above aldehyde (2 g) in tetrahydrofuran (35 ml) was added. The reaction mixture was stirred at room temperature overnight. Most tetrahydrofuran was removed, and the residue was taken up in ethyl acetate. The organic layer was washed with water, brine, and dried over magnesium sulfate. All solvents were removed, and the crude product was purified on silica gel using 15% ethyl acetate in hexane as eluent. The desired compound was isolated as a light yellow liquid (0.8 g).

EXAMPLE 14

2-[3-(1-Hydroxyethyl)phenoxymethyl]quinoline

A mixture of 3-(1-hydroxyethyl)phenol (7 g), 2-chloromethylquinoline (9 g), potassium carbonate (7 g) and potassium iodide (0.3 g) in acetone (75 ml) was refluxed overnight. The reaction mixture was poured into water, and then thoroughly extracted with ethyl acetate (3×30 ml). The organic extract was washed with NaOH solution (1N), water, brine, and then dried over MgSO$_4$. All volatiles were removed to obtain a dark brown liquid, which was chromatographed on silica gel (12% ethyl acetate in hexanes) to leave the desired product as a light yellow liquid.

EXAMPLE 15

2-[3-(1-N-methylaminohexyl)phenoxymethyl]quinoline

A solution of 2-[3-(hexanoyl)phenoxymethyl]quinoline (2.8 g), 40% aqueous methylamine (1.5 ml) and methanol adjusted to pH 6 with 5% aqueous hydrochloric acid is treated with a methanolic solution of sodium cyanoborohydride. The reaction is stirred overnight. The methanol is removed in vacuo and the remaining mixture is extracted with methylene chloride. The organic extract is dried (MgSO$_4$) and concentrated to an oil.

In like manner as above, using appropriate starting materials, the following compounds can be prepared:
2-[3-(1-n-butylaminohexyl)phenoxymethyl]quinoline; and
2-[3-(1-N,N-dimethylaninohexyl)phenoxymethyl]pyridine.

EXAMPLE 16

Preparation of starting compounds

A. 3-(1-Hydroxyhexyl)benzyl alcohol

To a solution of pentyl magnesium bromide (0.082 mol) in ethyl ether (100 ml) at 0° C., prepared as in Example 4, is added cadmium chloride (8.06 g) portionwise. The suspension is stirred overnight at room temperature. The solvent is distilled and toluene (300 ml) is added. The mixture is refluxed for one hour and cooled to room temperature. A solution of 3-carbomethoxy benzoyl chloride (48 g) in toluene (50 ml) is slowly added. The reaction is refluxed for two hours. After cooling, 3% aqueous hydrochloric acid is added. The organic phase is separated and the aqueous phase is extracted with ethyl acetate. The combined extracts are dried (MgSO$_4$) and concentrated to an oil. The oil is dissolved in ethyl ether and slowly added to a suspension of lithium aluminum hydride (4.0 g) in ethyl ether. The reaction is heated at reflux for two hours. The reaction was quenched by consecutive treatment with water (4 ml), 1N NaOH (12 ml) and water (4 ml). The mixture is filtered and the ethyl ether is removed in vacuo giving the desired product as a colorless liquid.

B. 3-(1-Hydroxyhexyl)benzyl p-toluene sulfonate

To a solution of 3-(1-hydroxyhexyl)benzyl alcohol (20.8 g) in pyridine (50 ml) is added paratoluenesulfonyl chloride (20.1 g). The reaction mixture is stirred at room temperature for two days. Ice is added and the mixture is extracted with ethyl ether (twice). The organic extract is washed with 5% aqueous hydrochloric acid (four times), brine, dried (MgSO$_4$) and concentrated to an oil.

EXAMPLE 17

2-[3-(1-Hydroxyhexylbenzylamino]pyridine

A mixture of 3-(1-hydroxyhexyl)benzyl p-toluenesulfonate (3.6 g), 2-aminopyridine (1.0 g) cesium carbonate (3.2 g) and toluene (200 ml) was heated at 70°–75° C. for two days. The reaction mixture was filtered and concentrated to an oil, which was purified by HPLC on silica gel.

In the same manner, using appropriate starting materials and reagents, the following compounds are prepared:
2-[3-(1-hydroxybutyl)anilinylmethyl]thiophene;
4-[3-(1-hydroxybutyl)anilinylmethyl]quinoline;
2-[2-(1-hydroxyhexyl)anilinylmethyl]quinoline;
3-methoxyphenyl-3-[1-(hydroxy)hexyl]benzyl thioether;
4-nitrophenyl-3-[1-(hydroxy)hexyl]benzyl thioether; and
methyl-2-[[3-(1-hydroxyhexyl)thiophenoxy]methyl]-benzoate.

EXAMPLE 18

N-[3-(1-Hydroxyhexyl)phenyl]pyridine-2-carboxamide

To a solution of pyridine-2-carboxylic acid chlorid (6.5 g) in methylene chloride (75 ml) was added a mixture of triethylamine (6.3 g) and 3-aminobenzaldehyde diethylacetal (9.75 g); (3-aminobenzaldehyde diethylacetal was prepared by reducing (H$_2$, Pd/C, MeHH) 3-nitrobenzaldehyde diethyl acetal, which in turn was made by acetalization of 3-nitrobenzaldehyde with triethylorthoformate and p-toluenesulfonic acid in ethanol). The mixture of the acid chloride and the primary amine was stirred at room temperature overnight, and poured carefully into cold water. The organic layer was separated, dried over anhydrous magnesium sulfate, and then all solvent removed. The residue was dissolved in tetrahydrofuran, and then dilute HCl solution (1N) was added until the acidic mixture remained homogeneous. This mixture was stirred at room temperature for one hour, and then most of the volatile solvent was removed. The aqueous solution was neutralized with NaHCO$_3$, extracted with ethyl acetate, and the organic extract was washed with water and brine. All volatiles were removed, and the residual solid was crystallized from methanol-hexanes to give N-(3-formyl-phenyl)-pyridine-2-carboxamide.

The aldehyde (1.1 g) was dissolved in dry tetrahydrofuran, and cooled in an ice bath. To this cold solution was added dropwise, a solution of pentylmagnesium bromide (prepared from 1-bromopentane (1.9 g) and magnesium turnings (0.31 g) in dry ether). The reaction mixture was stirred at 0° C. for two hours, allowed to warm to room temperature and was carefully poured into cold water. The aqueous solution was extracted with ethyl acetate, and the organic extract was washed with aqueous ammonium chloride solution, brine and then dried over anhydrous magnesium sulfate. All volatilss were removed to leave a viscous liquid which quickly solidified on standing. This solid was crystallized from ethyl acetate/hexane to give pure product.

EXAMPLE 19

2-[3-(2-hydroxy-2-heptyl)phenoxymethyl]quinoline

To an ethereal solution of 2-(3-hexanoylphenoxymethyl)quinoline (3.2 g) (prepared by oxidation of the corresponding alcohol with pyridinium chlorochromate in CH Cl) is added slowly an excess of a 3M solution of methylmagnesium bromide (2.5 g; 7.0 ml) in ether and the mixture stirred overnight. A saturated solution of ammonium chloride is added dropwise to the well-stirred reaction mixture until the solution became clear, and a gray-white solid coagulated to form a hard cake. The liquid was filtered, and the residue was washed with more ether. The ether layer was separated from the aqueous layer, washed with brine, and dried over magnesium sulfate. All volatiles were removed to give an oil, which was purified by chromatography on silica gel (6% ethyl acetate in hexane) to get the desired tertiary alcohol as a clear, colorless liquid.

In the same manner, using appropriate starting materials and reagents, the follownng compounds are prepared:
2-[3-(2-hydroxy-2-heptyl)phenoxymethyl]pyridine; and
2-[3-(1-hydroxy-2,2-dimethylbutyl)phenoxymethyl]quinoline.

EXAMPLE 20

A. 1-(2-Thienyl)-2-(3-hexanoylphenyl)ethylene

A mixture of α-bromo-m-tolunitrile (20 g) and triethylphosphite (29.1 g) is heated gently in a round bottomed flask fitted with a distilling head. Ethyl bromide that forms is removed by distillation. When no further ethyl bromide evolves, the residual liquid is distilled under reduced pressure to isolate the phosphonate as a clear, colorless liquid: 22 g, b.p. 152°-154° C./0.02 mm.

The phosphonate (22 g) is dissolved in dry tetrahydrofuran, and added dropwise to a well-stirred suspension of sodium hydride (4.2 g; 50% oil suspension) in dry tetrahydrofuran. After the addition is complete, the mixture is stirred at room temperature for one hour, cooled in an ice bath, and then a solution of 2-thiophenecarboxaldehyde (9.7 g) in dry tetrahydrofuran is added slowly. The mixture is allowed to warm up, and stirred at room temperature overnight. The excess of sodium hydride is destroyed by adding cold methanol, and then all volatiles are removed. The residue is taken up in ethyl acetate, and washed with HCl solution (5%) water and brine. The organic extract is dried and then all volatiles are removed to obtain the crude product, 1-(2-thienyl)-2-(3-cyanophenyl)ethylene.

To a solution of n-pentylmagnesium bromide (prepared from 1-bromopentane (7.3 g) and magnesium turnings (1.2 g) in tetrahydrofuran) is added a solution of the above cyano compound (8.1 g) in tetrahydrofuran. The resulting solution is refluxed for 8 hours. A solution of hydrochloric acid (6N) was added (24 ml) to the cold (0° C.) reaction mixture and again stirred at 40° C. for 8 hours. The mixture is cooled, and most tetrahydrofuran removed at the rotary evaporator. The residue is dissolved in ethyl acetate, and the organic extract washed with saturated sodium bicarbonate solution, brine, and then dried over magnesium sulfate. The solvent is removed to yield the crude product, which is purified by chromatography (silica gel; 3% ethyl acetate in hexane).

EXAMPLE 21

1-(2-Thienyl)-2-[3-(1-hydroxyhexyl) phenyl]ethylene

The ketone of Example 20 (1 g) is dissolved in ethanol, and sodium borohydride (0.2 g) is added. The mixture is stirred at room temperature overnight. Excess of the borohydride is destroyed by carefully adding a dilute HCl solution. The aqueous solution is extracted thoroughly with ether, and then the ether extract is washed with brine and dried. On removal of all volatiles, the pure alcohol is obtained as a clear, coloreess liquid in quantitative yield.

In the same manner as described in Examples 20 and 21, using the appropriate starting materials and reagents, the following compounds are prepared.
1-(2-quinolyl)-2-[3-(1-hydroxyhexyl)phenyl]ethylene;
1-(2-indolyl)-2-[3-(1-hydroxyhexyl)phenyl]ethylene; and
1-(2-furyl)-2-[3-(1-hydroxyhexyl)phenyl]ethylene.

EXAMPLE 22

A. 1-(2-Thienyl)-2-(3-hexanoylphenyl)acetylene

Bromine (6.4 g) is added to a solution of the cyano ethylene compound of Example 20 (7.4 g, 0.035 mol) in chloroform (75 ml) and the mixture stirred at room temperature overnight. The solution is washed with a 5% aqueous solution of sodium thiosulfate, water and then dried. On removal of all solvent, the desired dibromide is obtained as a solid. This crude dibromide is dissolved in dry tetrahydrofuran; potassium tert-butoxide (7.7 g) is added and the mixture refluxed overnight. Most solvent is removed and the residue taken up in ethyl acetate. The organic extract is washed with water, brine and dried. All solvent is removed to obtain the desired acetylenic compound, which is dissolved in ether. The acetylene product is crystallized from the ethereal solution.

Conversion of the cyano acetylene compound to the final product is accomplished as described in Example 20.

B.

1-(2-Thienyl)-2-[3-(1-hydroxyhexyl)phenyl]acetylene

This product is obtained from the product of paragraph A by the procedure of Example 21.

Using the procedures of paragraphs A and B, the following compounds are prepared:
1-(2-quinolyl)-2-[3-(1-hydroxyhexyl)phenyl]acetylene
1-(2-indolyl)-2-[3-(1-hydroxyhexyl)phenyl]acetylene
1-(2-furyl)-2-[3-(1-hydroxyhexyl)phenyl]acetylene; and
the corresponding ketones from which they are prepared.

EXAMPLE 23

2-[3-(1-Methoxyhexyl)phenoxymethyl]quinoline

To a suspension of sodium hydride (0.5 g) in ethyl ether at 0° C. is added 2-[3-(1-hydroxyhexyl)phenoxymethyl]quinoline (1.8 g) in ether. The mixture is allowed to warm to room temperature. Methyl iodide (0.6 ml) is added and the reaction is stirred at room temperature for three days. The reaction mixture is quenched with saturated aqueous ammonium chloride and extracted with ethyl ether. The organic extract is washed with water, dried ($MgSO_4$) and concentrated to an oil, which is purified by HPLC on silica gel using a 1:9 ratio of ethyl acetate/hexane as an eluent.

Other alkyl ethers of the corresponding new alcohols of the invention are prepared using lower alkyl iodides in lieu of methyl iodide (as desired) employing this procedure. Benzyl ether are similarly prepared using the corresponding bromides. Phenyl ethers are prepared similarly from the corresponding benzylic bromides and phenol.

EXAMPLE 24

2-[3-(1-Acetoxyhexyl)phenoxymethyl]quinoline

To a solution of 2-[[3-(1-hydroxyhexyl)phenoxymethyl]quinoline (1.7 g) in pyridine at 0° C. was added acetic anhydride (2.7 ml). The reaction mixture was stirred overnight at room temperature. The solvent was removed in vacuo to obtain the crude product.

Similarly, corresponding new alcohols of the invention are acetylated with lower alkanoic acid anhydrides or chlorides to obtain the lower alkanoyl derivatives.

EXAMPLE 25

3-(3-(1-Hydroxyhexyl)phenoxymethyl)quinoline

To a solution of 3-chloromethylquinoline (10 g, 0.056 mol; prepared from 3-hydroxymethylquinoline and thionyl chloride) and 3-(1-hydroxyhexyl)phenol (12 g, 0.062 mol) in DMSO (200 ml) was added a 2N solution of sodium hydroxide (31 ml, 0.062 mol). The solution became warm (40°–45° C.). This was allowed to stir at room temperature for 5 hours. The dark reaction mixture was poured into water, and the aqueous solution was thoroughly extracted (4×50 ml) with ethyl acetate. The organic extract was washed with 1N NaOH solution, water and then brine. After drying over anhydrous magnesium sulfate, all volatiles were removed. The dark residual liquid on trituration with ether-petroleum ether (1:2) yielded a beige colored solid, which on recrystallization from hexane-ethyl acetate gave the desired material (12.9 g, 69%) as an off-white solid.

In a similar manner, starting from 6-chloromethylquinoline and 3-(1-hydroxyhexyl)phenol, the other isomeric compound,6-(3-(1-hydroxyhexyl)phenoxymethyl) quinoline, can be prepared.

EXAMPLE 26

2-(3-(1-Hydroxy-5,5,5-trifluoropentyl)phenoxymethyl)-quinoline

To a solution of sodium 3-formylphenolate (prepared from 3-hydroxybenzaldehyde (6.2 g, 0.051 mol) and sodium hydride (1.25 g, 0.052 mol))in dry THF (150 ml) was added dropwise a solution of 4,4,4-trifluorobutyl magnesium bromide (made from 1-bromo-4,4,4-trifluorobutane (10 g, 0.052 mol; b.p. 95°–101° C.) and magnesium turnings (1.27 g, 0.052 mol)) in THF (100 ml) under vigorous stirring. After the addition of the Grignard reagent was complete (20 min.), the reaction mixture was warmed to about 40° C., and stirred at this temperature for about 3 hours. The mixture was cooled in an ice bath, and quenched with a saturated solution of ammonium chloride. The organic layer was separated, washed with brine, and dried over magnesium sulfate. All volatiles were removed to leave the crude desired phenol (9 g) which was pure enough to be used without further purification.

This crude phenol (9 g) and 2-chloromethylquinoline (7.6 g) were dissolved in DMSO (80 ml), and then 2N sodium hydroxide solution (20 ml) was added.

The reaction mixture was stirred at room temperature overnight, poured into water, and then the aqueous solution was extracted with ethyl acetate (3×50 ml). The organic extract was washed with 1N NaOH solution, water, 0.1N HCl solution, water and brine. After drying the organics over $MgSO_4$, all volatiles were removed to obtain a dark liquid, which was chromatographed on silica gel (20% ethyl acetate in hexanes). The pure material was crystallized from ether to give the desired ether as a light yellow solid (m.p. 89°–91° C.).

EXAMPLE 27

2-(3-(2-Quinolinylmethoxy)phenoxy)propionic acid (hydrochloride salt)

Ethyl 2-(3-(2-quinolinylmethoxy)phenoxy)propionate (3.6 g; m.p. 58°–60° C.) was taken up in 10% hydrochloric acid solution (180 ml), and the mixture was heated at 100° C. for 26 hours. On cooling the reaction mixture in an ice bath, the desired carboxylic acid crystallized as a hydrochloride salt (3.6 g), which was recrystallized from ethanol to give the desired acid, as its hydrochloride salt, as colorless crystals, (2.2 g; m.p. 184°–185° C.).

In a similar manner, starting from ethyl 2-(3-(2-quinolinylmethoxy)phenoxy propionate (2.5 g) and hydrochloric acid (90 ml, 4N), 2-(3-(2-quinolinylmethoxy)phenoxypropionic acid (hydrochloride salt; 1.3 g; m.p. 136°–138° C.) can be prepared.

EXAMPLE 28

2-(3-(1-Hydroxyhexyl)benzyloxymethyl)quinoline

A mixture of 2-hydroxymethylquinoline (8 g, 0.05 mol) and 3-(1-hydroxyhexyl)benzyl p-toluenesulfonate (18.2 g, 0.05 mol; prepared as in Example 17) in methylene chloride (200 ml) containing triethylamine (15 ml) was stirred at 0° C. for 4 hours, and then allowed to warm up to room temperature. This mixture was stirred for two more hours at this temperature, and then poured into water. The organic layer was separated and washed with dilute sodium hydroxide solution, water and brine. After drying the organics, all volatiles were removed to obtain the crude product as a yellowish brown liquid. This was purified by chromatography on silica gel using 15% ethyl acetate in hexanes to get the pure product as a clear, light yellow liquid (9 g, 52% yield).

EXAMPLE 29

2-[3-(6-(3-chlorophenoxy)-1-hydroxyhexyl)phenoxymethyl]quinoline

A mixture of 2-chloromethyl quinoline (2.77 g, 15.6 mmol) 3-hydroxy-1-(6-(3-chlorophenoxy)-1-hydroxyhexyl) benzene (5.0 g, 15.6 mmol) and finely powdered anhydrous potassium carbonate (4.3 g, 31.2 mmol) in acetone (85 ml) containing catalytic amounts of finely powdered, anhydrous cesium carbonate (0.5 g, 1.5 mmol) and sodium iodide (0.01 g, 0.67 mmol) was refluxed overnight (12 hours). The reaction mixture was cooled to room temperature, and filtered. The solid residue was washed thoroughly with acetone (3×15 ml), and all the filtrates were combined. All volatiles were removed from the combined acetone filtrate to leave a light yellow viscous liquid which solidified to an off-white solid on trituration with a 1:1 mixture of ether and petroleum ether (35°-55° C.). This solid was crystallized from ethyl acetate-ether mixture to yield the desired product (3 g, 42%) as a white crystalline solid, m.p. 69.5°-70.5° C. Anal. Calcd. for $C_{28}H_{28}ClNO_3$: C, 72-79; H, 6.11; N, 3.03. Found: C, 72.59; H, 6.16; N, 2.81.

In a similar manner, the following compounds can be made:
2-[3-(6-phenoxy)-3-1-hydroxyhexyl)phenoxymethyl]-quinoline;
2-[3-(6-(3-trifluoromethylphenoxy)-1-hydroxyhexyl)-phenoxymethyl]quinoline.

EXAMPLE 30

3-[6-(3-chlorophenoxy)-1-hydroxyhexyl]phenol

To a gently refluxing dry tetrahydrofuran (75 ml) containing magnesium turnings (1.3 g; 53 mmol) and a small crystal of iodine, was added dropwise from a dropping funnel a solution of 5-(3-chlorophenoxy)pentyl bromide (13.87 g, 50 mmol) in dry THF (55 ml). After about 5-7 minutes, the Grignard reaction started as indicated by the disappearance of the brown iodine color. The heating was adjusted so that the solution refluxed gently. After the addition of the halide was complete (ca. 30 min.), the clear solution was refluxed for about 1 hour. This solution of the Grignard reagent was cooled to room temperature. A solution of 3-hydroxybenzaldehyde (5.5 g, 45 mmol) in dry THF (50 ml) was added dropwise to a well-stirred suspension of sodium hydride (2.8 g, 58 mmol) (50% oil dispersion) in dry THF (75 ml) at room temperature. The temperature was not allowed to go above ca. 40° C. After the addition of 3-hydroxybenzaldehyde was complete (ca. 30 min.) the slightly cloudy solution was warmed to 45°-50° C., and the stirred for 1 hour at this temperature. The resulting clear solution of sodium 3-formyl phenoxide was cooled to room temperature, and added dropwise, using a cannula, to the well-stirred solution of the Grignard reagent (whose preparation was described above). A thick precipitate immediately formed, and the solution was difficult to stir. This reaction mixture was maintained 40°-45° C. during the addition of the sodium salt. After the addition was complete (ca. 2 hours), the reaction mixture was stirred at this temperature for another hour, and then cooled in an ice bath. The excess reactive materials (sodium hydride, Grignard reagent, etc.) were destroyed slowly by carefully adding methanol (30 ml), and then a saturated ammonium chloride solution (350 ml) was added to dissolve all solids. The organic layer was separated, and the aqueous layer was extracted with ether (2×75 ml). The combined organics were washed with water, brine, and then dried over anhydrous magnesium sulfate. After drying the extract, all volatiles were removed to obtain a dark liquid. This oil was triturated with a 1:1 mixture of ether and petroleum ether (35°-55° C.) until an off-white solid was obtained (11.1 g; 78% yield). This can be crystallized from methanolethyl acetate to give a white solid, m.p. 125°-127° C.; mass spectrum: m/e (intensity observed at 320 (86.9%) and 322 (29.5%) which correspond to the molecular ion. The crude material was, however, pure enough to be used for the next reaction.

Similarly, the following compounds can be made:
3-[6-phenoxy-1-hydroxyhexyl]phenol;
3-[6-(3-trifluoromethylphenoxy)-1-hydroxyhexyl]-phenol

EXAMPLE 31

2-[3-(6-Phenoxy-1-hydroxy-1-methylhexyl)phenoxymethyl]quinoline

To a gently refluxing dry tetrahydrofuran (100 ml) containing magnesium turnings (0.5 g, 21 mmol) and a small crystal of iodine, was added dropwise pure 5-phenoxypentyl bromide (5.0 g, 21 mmol; b.p. 118°-125° C./1 mm). After a few minutes, the reaction started, and the iodine color disappeared. The addtion of the bromide continued at such a rate as to maintain a gentle reflux. After the addition was oomplete (ca. 20 min.), the solution was refluxed for another 30 min., and then cooled. This cold Grignard solution was next added dropwise via a cannula to an ice cold solution of 3-(2-quinolinylmethoxy)acetophenone (5 g, 18 mmol) in dry THF (100 ml). After the addition was complete (ca. 45 min.), the ice bath was removed, and the solution was slowly heated to mild reflux for 3 hours. (The reaction was rather slow at room temperature.) The reaction mixture was cooled in an ice bath, and a saturated ammonium chloride solution was added to it. The organic layer was separated, washed with brine, and dried over anhydrous magnesium sulfate. All volatiles were removed to give a crude oily reaction mixture which was purified by chromatography (HPLC on silica gel, 20% ethyl acetate in hexanes used as eluent). The desired alcohol (Rf 0.2) was obtained as a pale yellow lqquid (2.6 g, 33%). Anal: Calcd. for $C_{29}H_{31}NO_3$: C, 78.88; H, 7.08; N, 3.17. Found: C, 78.76; H, 7.19; N, 3.05.

In an analogous manner, the following compounds can be synthesized:
2-[3-(6-(3-chlorophenoxy)-1-hydroxy-1-methylhexyl)-phenoxymethyl]quinoline;
2-[3-(6-(3-trifluoromethylphenoxy)-1-hydroxy-1-methylhexyl)phenoxymethyl]quinoline.

EXAMPLE 32

3-(2-quinolinylmethoxy)acetophenone

A mixture of 2-chloromethyl quinoline (25 g, 0.14 mol), 3-hydroxyacetophenone (21.1 g, 0.155 mol), finely powdered anhydrous potassium carbonate (30 g, 0.22 mol) and a catalytic amount of dry powdered potassium iodide (1 g) in acetone (300 ml) was refluxed overnight. The solution was filtered and the residue was washed with acetone (2×25 ml). All volatiles were removed from the combined filtrate to leave the crude oily reaction mixture. This oil was taken up in ethyl acetate (150 ml) and the organic extract was washed with a 5% sodium hydroxide solution (3×30 ml). The ethyl acetate solution was washed with water, brine and then dried. On removal of all volatiles, a light yellow liquid was obtained, which on trituration with petroleum ether (35°-55° C.) gave a beige solid (37 g, 95% yield) m.p. 93°-95° C., which was the desired product, pure enough to be used in the next step.

EXAMPLE 33

3-(2-Quinolinylmethoxy)phenylacetic acid

A mixture of 2-chloromethyl quinolin (2.3 g, 13.3 mmol), 3-hydroxyphenyl acetate (2.2 g, 13.3 mmol), excess powdered potassium carbonate (10 g) and a catalytic amount of potassium iodide (0.1 g) in dry acetone (150 ml) was refluxed overnight (18 hr.). The reaction mixture was filtered, and the filtrate was concentrated, taken up in ethyl acetate, and the organic extract was washed with a 5% NaOH solution and brine. After drying over $MgSO_4$, all volatiles were removed from the organic extract, and the crude oil was chromatographed on silica gel (20% ethylacetate in hexanes) to obtain the methyl ester of the desired product (3.0 g).

The above ester (3.0 g) was dissolved in 4N HCl solution, and this was refluxed for 4 hours. On cooling in an ice bath, the product crystallized out as the hydrochloride salt. This salt was purified further by recrystallization twice from ethanol. The desired product was obtained as the hydrochloride salt, as slightly pink crystals (2.5 g), and slowly decomposes with melting above 180° C.

EXAMPLE 34

2-(3-(6-Phenoxy-1,2,2-trimethyl-1-hydroxyhexyl)-phenoxymethyl) quinoline

To a solution of the ketone, 2-(3-(6-phenoxy-2,2-dimethyl hexanoyl)phenoxymethyl) quinoline (3.6 g) in dry ether (100 ml) at 0° C., was added dropwise, an ethereal solution of methyl magnesiumbromide (7.7 ml, 23.8 mmol, 3 eqv.) under an atmosphere of nitrogen. The clear orange solution was stirred overnight at room temperature. To this solution, a saturated ammonium chloride solution was added when the magnesium salts precipitated. The ether layer was separated, washed with water and brine, and then dried over $MgSO_4$. All volatiles were removed to obtain the crude product (4.2 g). This was purified by chromatography on silica gel (25% ethyl acetate in hexanes, 20% ethyl acetate in hexanes and finally 10% ethyl acetate in hexanes) to obtain the pure product as a yellow liquid (0.9 g).

EXAMPLE 35

2-(3-Hexylphenoxy)methyl quinoline

A solution of 99% pure 2-(3-(1-hexenylphenoxy) methyl) quinoline (1.5 g) in ethanol (20 ml) containing 10% Pd-C catalyst (0.5 g) was exposed to an atmosphere of hydrogen at 10 psig for one hour. The catalyst was filtered through a bed of celite, and all ethanol was removed to obtain the pure desired saturated compound (1.1 g) as a yellow liquid.

EXAMPLE 36

1-(3-(2-Quinolinylmethoxy)phenyl)-3-methyl-1,3-butane diol

A mixture of 2-chloromethyl quinoline hydrochloride (10 g, 47 mmol), 3-hydroxybenzaldehyde (6.3 g, 52 mmol), powdered potassium carbonate (14.5 g, 105 mmol), catalytic amounts of cesium carbonate (1.5 g) and sodium iodide (0.7 g) in dry acetone (150 ml) was refluxed for 14 hours. The solid residue was filtered off, and the filtrate was concentrated and dissolved in ethyl acetate. The organic solution was washed successively with 10% NaOH solution water and brine and then dried over $MgSO_4$. All volatiles were removed to leave a yellowish solid weighing 14.8 g. This was recrystallized from hexanes-ethanol mixture to obtain 4-(3-(2-quinolinylmethoxy)phenyl-4-hydroxy-2-butanone as off-white crystals (11.8 g), mp 116°-9° C.

To a solution of the above hydroxy-ketone (2.5 g) in dry THF (150 ml) was added dropwise, an ethereal solution of methyl magnesium bromide (17.1 mmol, 2.2 eqv.). The reaction mixture was stirred overnight, and then a saturated ammonium chloride solution was added. The precipitated magnesium salts were filtered, and the filtrate was concentrated in vacuo. The desired material was isolated after purification by chromatography on silica gel using 40% ethyl acetate in hexanes, as a yellowish crystalline solid, mp 117°-124° C. (1.2 g).

EXAMPLE 37

2-(3-(6,6,6-Trifluorohexanoyl)phenoxymethyl) quinoline

A mixture of 3-(6,6,6-trifluorohexanoyl)phenol (6.8 g, 27 mmol) and 2-chloromethylquinoline (4.4 g, 25 mmol) in DMSO (75 ml) containing 2N NaOH solution (14 ml) was stirred at room temperature overnight (13 hrs.). The dark reaction mixture was poured into water (200 ml) and the aqueous solution was extracted with ethyl acetate (4×30 ml). The organic extract was washed with 1N NaOH solution, water and brine and then dried over $MgSO_4$. After removal of all volatiles, a dark liquid was obtained which solidified on standing (7.2 g). This solid was chromatographed (3% ethanol in toluene on silica gel) to obtain a beige color solid (4.5 g; mp 83°-4° C.), which was chromatographed again (15% acetone in hexanes on silica gel) to get a white solid (3.1 g; mp 86°-87° C.). This pure material was recrystallized from hexanes-acetone (trace) to leave the desired compound as a colorless, crystalline solid (2.4 g), mp 88°-88.5° C. (first crop; second crop mp 87°-88° C.).

EXAMPLE 38

2-(3-(5,5,5-Trifluoropentanoyl)phenoxymethyl) quinoline

This material was synthesized by refluxing a mixture of 2-chloromethyl quinoline (2.6 g, 14.5 mmol), 3-(5,5,5-trifluoropentanoyl)phenol (3.7 g, 15.9 mmol), powdered potassium carbonate (6.0 g, 43.5 mmol) and a catalytic amount of potassium iodide (0.1 g) in dry acetone (50 ml) for 14 hours. After this period, the mixture was filtered, and the filtrate was concentrated. The residue was dissolved in ether, and the ethereal solution was washed with brine, dried over $MgSO_4$, and then concentrated in vacuo. The pure desired ketone was isolated by chromatography on silica gel using 20% ethyl acetate in hexanes as eluent. The product was obtained in 62% yield (3.4 g), had a melting point 80°-82° C. and was a yellowish solid.

EXAMPLE 39

2-(3-(6-Benzyloxy-1-hydroxyhexyl)phenoxymethyl) quinoline

2-Chloromethyl quinoline (3.6 g) was refluxed with 3-(6-benzyloxy-1-hydroxyhexyl)phenol (4.2 g), powdered potassium carbonate (8 g) and potassium iodide (0.2 g) in dry acetone (150 ml) overnight (16 hrs.). The suspension was filtered, the filtrate was concentrated in vacuo and then taken up in ethyl acetate. This solution was washed with 5% NaOH solution, water and brine and then dried. All solvent was removed to obtain the crude product which was purified by chromatography (silica gel; 30% ethyl acetate in hexanes). The pure compound was dissolved in ether, and was precipitated as the hydrochloride salt with a dry ethereal solution of HCl. The pure salt was filtered, washed with cold water, and dried in vacuo to yield a tan powder (1.5 g), mp 86°–89° C.

EXAMPLE 40

Methyl 3-(3-(2-quinolinylmethoxy)benzoyl)propanoate

A mixture of pure methyl 4-(3-(2-quinolinylmethoxy)phenyl-4-hydroxy butyrate (1.1 g) and activated manganese dioxide (6.2 g) in methylene chloride (25 ml) was stirred at room temperature. After 20 hours, no starting material was detected by thin layer chromatogaaphy. The manganese dioxide was filtered through celite, and the methylene chloride solution was concentrated in vacuo. The residue was purified by chromatography on silica gel using 15% ethyl acetate in hexanes containing 1% acetic acid as eluent. The desired keto-ester was obtained (0.22 g) as an off-white solid, mp 80°–81° C.

EXAMPLE 41

Synthesis of 5-phenoxypentyl bromide

To a well-stirred suspension of sodium hydride (15.3 g, 0.32 mol; 50% oil dispersion) in dry DMF (500 ml) containing (25 g, 0.26 mol), was added dropwise 1,5-dibromopentane (122.3 g, 0.53 mol). After the addition was complete, the reaction mixture was stirred at 60°–70° C. for 4 hours. Most of the DMF was next removed under reduced pressure, and the residue was dissolved in ethyl acetate (250 ml). The organic extract was washed successively with a 5% sodium hydroxide solution, water and brine. After drying the organics over anhydrous magnesium sulfate, all volatiles were removed. The residual yellow liquid was then distilled under reduced pressure, and the pure product was collected at 118°–125° C./1 mm as a clear colorless liquid (26 g, 40% yield).

Synthesis of 3-(6-phenoxy-1-hydroxyhexyl)phenol

To gently refluxing dry tetrahydrofuran (70 ml) containing magnesium turnings (1.1 g, 45 mmol) and a small crystal of iodine, was added dropwise from a dropping funnel a solution of 5-phenoxypentyl bromide (11.0 g, 45 mmol) in dry THF (50 ml). After about 5–7 minutes, the Grignard reaction started as indicated by the disappearance of the brown iodine color. The heating was adjusted so that the solution refluxed gently. After the addition of the halide was complete (ca. 30 min.), the clear solution was refluxed for about 1 hour. This solution of the Grignard reagent was cooled to room temperature.

A solution of 3-hydroxybenzaldehyde (5.0 g, 41 mmole) in dry THF (50 ml) was added dropwise to a well-stirred suspension of sodium hydride (2.5 g, 52 mmol; 50% oil dispersion) in dry THF (50 ml) at room temperature. The temperature was not allowed to go above ca. 40° C. After the addition of 3-hydroxybenzaldehyde was complete (ca. 30 min.) the slightly cloudy solution was warmed to 45°–50° C. and stirred for 1 hour at this temperature. The resulting clear solution of sodium 3-formyl phenoxide was cooled to room temperature and added dropwise using a cannula, to the well-stirred solution of the Grignard reagent (whose preparation was described above). A thick precipitate immediately formed. This mixture was maintained at 40°–45° C. during the addition of the sodium salt. After the addition was complete (ca. 2 hours), the reaction mixture was stirred at this temperature for another hour, and then cooled in an ice bath. The excess reactive materials (sodium hydride, Grignard reagent, etc.) were dsstroyed slowly by carefully adding methanol (30 ml), and then a saturated ammonium chloride solution (350 ml) was added to dissolve all solids. The organic layer was separated, and the aqueous layer was extracted with ether (2×75 ml). The combined organics were washed with water, brine, and then dried over anhydrous magnesium sulfate. After drying the extract, all volatiles were removed to obtain a dark liquid. This oil was triturated with a 1:1 mixture of ether and petroleum ether (35°–55° C.) when an off-white solid was obtained (12 g). This can be crystallized from methanol-ethyl acetate to give a white solid, mp 148°–9° C.

Synthesis of 2-[3-(6-phenoxy-1-hydroxyhexyl)phenoxymethyl]-quinoline

A mixture of 2-chloromethyl quinoline (1.1 g; 6.3 mmol), 3-(6-phenoxy-1-hydroxyhexyl)phenol (1.8 g, 6.3 mmol) and finely powdered anhydrous potassium carbonate (1.74 g, 12.6 mmol) in acetone (40 ml) containing catalytic amounts of finely powdered, anhydrous cesium carbonate (0.4, 1.3 mmol) and sodium iodide (0.05 g, 0.33 mmol) was refluxed overnight (15 hours). The reaction mixture was cooled to the room temperature and filtered. The solid residue was washed thrroughly with acetone (3×15 ml), and all the filtrates were combined. All volatiles were removed from the combined acetone filtrate to leave a light yellow viscous liquid which solidifed to an off-white solid on trituration with a 1:1 mixture of ether and petroleum ether (35°–55° C.). This solid was chromatographed on silica gel with 35% ethylacetate in hexanes to yield the desired product (1.6 g, 60%) as a white crystalline solid, mp 83°–84.5° C.

TABLE I

| | Ar₁—X—Ar—Z—(R)ₙ' | | | |
|---|---|---|---|---|
| Ar₁ | X | Ar | Z(R)ₙ' | 5-LOX I₅₀ μM |
| 2-quinolyl | —CH₂O— | C₆H₄ | 3-(CHC₅H₁₁)<br>    \|<br>    OH | 0.16 |
| 2-quinolyl | —CH₂O— | C₆H₄ | 3-(C(CH₃)C₅H₁₁)<br>    \|<br>    OH | 0.1 |
| 2-pyridyl | —CH₂O— | C₆H₄ | 3-(—CHC₅H₁₁)<br>    \|<br>    NHCH₃ | 2.2 |
| 2-quinolyl | —CH₂O— | C₆H₄ | 3-(—CH=CHC₄H₉) | 2.4 |
| 2-quinolyl | —CH₂O— | C₆H₄ | 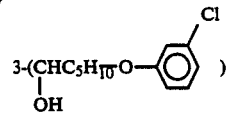 | 0.6 |
| 2-quinolyl | —CH₂O— | C₆H₄ | 3-(CH—C₅H₁₀OC₆H₅)<br>    \|<br>    OH | 0.6 |
| 2-quinolyl | —CH₂O— | C₆H₄ | 3-(C(CH₃)C₅H₁₀OC₆H₅)<br>    \|<br>    OH | 0.8 |
| 2-quinolyl | —CH₂O— | C₆H₄ | 3-(CHCH(CH₃)C₄H₉)<br>    \|<br>    OH | 0.2 |

TABLE I-continued $Ar_1-X-Ar-Z-(R)_{n'}$

| $Ar_1$ | X | Ar | $Z(R)_{n'}$ | 5-LOX $I_{50}$ μM |
|---|---|---|---|---|
| 2-quinnolyl | $-CH_2O-$ | $C_6H_4$ | 3-(CHC(CH$_3$)$_2$C$_4$H$_9$)<br>  \|<br>  OH | 0.27 |
| 2-quinolyl | $-CH_2O-$ | $C_6H_4$ | 3-(C(CH$_3$)C(CH$_3$)$_2$C$_4$H$_9$)<br>  \|<br>  OH | 0.27 |
| 2-quinolyl | $-O-$ | $C_6H_4$ | 4-(CH—C$_5$H$_{11}$)<br>  \|<br>  OH | 0.35 |
| 4-pyridyl | $-CH_2O-$ | $C_6H_4$ | 3-(CHC$_5$H$_{11}$)<br>  \|<br>  OH | 3 |
| 2-pyridyl | $-CH_2O-$ | $C_6H_4$ | 3-(CHC$_5$H$_{11}$)<br>  \|<br>  OH | 0.5 |
| 3-pyridyl | $-CH_2O-$ | $C_6H_4$ | 3-(CHC$_5$H$_{11}$)<br>  \|<br>  OH | 3 |
| 6-(2-carboxypyridyl) | $-CH_2O-$ | $C_6H_4$ | 3-(CHC$_5$H$_{11}$)<br>  \|<br>  OH | 1.9 |
| 6-(2-cyanopyridyl) | $-CH_2O-$ | $C_6H_4$ | 3-(CHC$_5$H$_{11}$)<br>  \|<br>  OH | 30 |
| 2-quinolyl | $-CH_2O-$ | $C_6H_4$ | 3-(CC$_5$H$_{11}$)<br>  \|\|<br>  O | 0.15 |
| 2-pyridyl | $-CH_2O-$ | $C_6H_4$ | 3-(C(CH$_3$)C$_5$H$_{11}$)<br>  \|<br>  OH | 0.3 |
| 2-quinolyl | $-CH_2O-$ | $C_6H_4$ | 3-(CHCH$_2$CCH$_3$)<br>  \|      \|\|<br>  OH  O | 0.18 |
| 2-quinolyl | $-CH_2O-$ | $C_6H_4$ | 4-(CHC$_5$H$_{11}$)<br>  \|<br>  OH | 0.35 |

Using the procedures of the foregoing examples, the following compounds are prepared:

2-[3-(1-hydroxyhexyl)phenoxymethyl]quinoline;
2-[3-(1-methyl-1-hydroxyhexyl)phenoxymethyl]quinoline;
2-[3-(1,2-dihydroxyhexyl)phenoxymethyl]quinoline;
2-[3-(2,2-dimethyl-1-hydroxyhexyl)phenoxymethyl]pyridine;
2-[3-(1,2,2-trimethyl-1-hydroxyhexyl)phenoxymethyl]quinoline;
2-[3-(1-methyl-1-hydroxyhexyl)phenoxymethyl]pyridine;
2-[3-(6-[3-chlorophenoxy]-1-hydroxyhexyl)phenoxymethyl]quinoline;
2-[3-(6-phenoxy-1-hydroxyhexyl)phenoxymethyl]quinoline;
2-[3-(6-phenoxy-2,2-dimethyl-1-hydroxyhexyl)phenoxymethyl]quinoline
2-[3-(6-[3-trifluoromethylphenoxy]-1-hydroxyhexyl)phenoxymethyl]quinoline;
2-[3-(1-hydroxyhexyl)phenoxymethyl]benzofuran;
2-[5-(1-hydroxyhexyl)-2-furyloxy)methyl]pyridine;
4-[5-(1-hydroxyhexyl)-2-thienylmethoxy]quinoline;
2-[6-(1-hydroxyhexyl)-3-pyridyloxy]quinoline;
3-[3-(1-hydroxyhexyl)phenoxymethyl]pyridine;
2-[3-(1-hydroxyethyl)benzylthio]pyridine; and
2-[3-(6-[3-chlorophenoxy]-1-methyl-1-hydroxyhexyl)-phenoxymethy]quinoline;
2-(3-(1-hydroxy-2,2-dimethyl-5,5,5-trifluoropentyl)-phenoxymethyl)quinoline;
2-(3-(1,2,2,-trimethyl-5,5,5-trifluoro-1-hydroxypentyl)-phenoxymethyl)quinoline;
2-(3-(2,2-dimethyl-6,6,6-trifluoro-1-hydroxyhexyl)-phenoxymethyl)quinoline;
2-(3-(1,2,2-trimethyl-6,6,6-trifluoro-1-hydroxyhexyl)-phenoxymethyl)quinoline;
2-(3-(2,2-dimethyl-6,6,6-trifluoro-1-hydroxyhexyl)-phenoxymethyl)pyridine;
3-(3-(2,2-dimethyl6,6,6-trifluoro-1-hydroxyhexyl)-phenoxymethyl)pyridine;
4-(3-(2,2-dimethyl-6,6,6-trifluoro-1-hydroxyhexyl)-phenoxymethyl)quinoline;
2-(3-(6-methoxyhexyl)phenoxymethyl)quinoline;
2-(3-(4-methoxybutyl)phenoxymethyl)quinoline;
2-(4-(4-methoxybutyl)phenoxymethyl)quinoline;
2-(3-(6-phenoxyhexyl)phenoxymethyl)quinoline;
2-(3-(4-methoxybutyl)phenoxy)quinoline;
2-(3-(1,1,1-trimethylacetoxyhexyl)phenoxymethyl)-quinoline;
2-(3-(1-acetoxy-5,5,5-trifluoropentyl)-phenoxymethyl)-quinoline;
2-(3-(1,1,1-trimethylacetoxy-5,5,5-trifluoropentyl)-phenoxymethyl)quinoline;
2-(3-(1,1,1-trimethylacetoxy-6,6,6-trifluorohexyl)-phenoxymethyl)quinoline;
2-(3-(2,2-dimethyl-1,1,1-trimethylacetoxyhexyl)-phenoxymethyl)quinoline;
2-(3-(2,2-dimethyl-6,6,6-trifluoro-1,1,1-trimethylacetoxyhexyl)phenoxymethyl)quinoline;
3-(3-(2-quinolinylmethoxy)benzoyl)propanoic acid;
5-(3-(2-quinolinylmethoxy)benzoyl)pentanoic acid;
methyl 5-(3-(2-quinolinylmethoxy)benzoyl) pentanoate;
methyl 4-(3-(2-quinolinylmethoxy)phenyl)-4-hydroxy butyrate;
4-(3-(2-quinolinylmethoxy)phenyl)-4-hydroxy butyric acid (and the corresponding lactone);
methyl 6-(3-(2-quinolinylmethoxy)phenyl-6-hydroxy hexanoate;
6-(3-(2-quinolinylmethoxy)phenyl)-6-hydroxy hexanoic acid (and the corresponding lactone);
5-(3-(2-quinolinylmethoxy)phenyl)-5-hydroxy pentanoic acid (and the corresponding lactone);
methyl 5-(3-(2-quinolinylmethoxy)phenyl)-5-hydroxy pentanoate;
methyl 4-(3-(2-quinolinylmethoxy)benzoyl)butyrate;
4-(3-(2-quinolinylmethoxy)benzoyl)butyric acid;
6-(3-(1-hydroxyhexyl)phenoxymethyl)-1,4-benzodioxan;
2-(3-(1-hydroxyhexyl)phenoxymethyl)-1,4-benzodioxan;
2-(3-(1-hydroxyhexyl)phenoxymethyl)quinoxaline;
2-(3-(1-hydroxyhexyl)phenoxymethyl)-3-methyl quinoxaline;
7-(3-(1-hydroxyhexyl)phenoxymethyl)-5-methyl-1,8-naphthyridin-2-ol;
2-(3-(1-hydroxy-6-phenoxyhexyl)phenoxymethyl)-quinoxaline;
2-(3-(1-hydroxy-6-phenoxyhexyl)phenoxymethyl)-1,5-naphthyridine;
2-(3-(1-hydroxy-6-phenoxyhexyl)phenoxymethyl)-1,6-naphthyridine;
2-(3-(1-hydroxyhexyl)phenoxymethyl)pyrido(2,3-b)pyrazine;

2-(3-(1-hydroxy-6-phenoxyhexyl)phenoxymethyl)-pyrido(3,4-b) pyrazine;
2-(3-(1-hydroxyhexyl)phenoxymethyl)pyrido(3,4-d)pyrimidine;
2-(3-(1-hydroxy-6-phenoxyhexyl)phenoxymethyl)-pyrido(4,3-d) pyrimidine;
3-(3-(1-hydroxyhexyl)phenoxymethyl)piperazine-2,5-dione; and
3-(3-(6-phenoxy-1-hydroxyhexyl)phenoxymethyl)-2,5-dimethoxy-3,6-dihydropyrazine.

What is claimed is:

1. A compound of the formula:

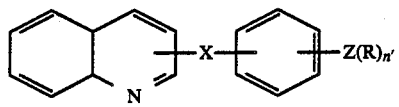

where the quinolyl or phenyl ring contains one to three substituents selected from the group hydrogen, lower alkyl of up to 6 carbon atoms, phenyl halo, hydroxy, trifluoromethyl, carboxy, formyl, nitrilo, amino, carboxamide, phenoxy nitro, sulfonyl, sulfonamide, thio or wherein

X=

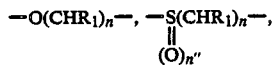

Z is an aklylene chain containing up to 10 carbon atoms in the principle chain and a total of up to 12 carbon atoms and from 0 to 2 double bonds;
each R is a substituent, attached to one of the carbon atoms of Z selected from the group consisting of =O, OR$_3$, SR$_3$,
R$_1$ is H or CH$_3$;
R$_2$ is H, C$_1$ to C$_6$ alkyl, phenyl or benzyl;
n=0 or 1;
n'=1 or 2;
n"=0, 1 or 2.

2. The compound according to claim 1 which is 2-[3-(1-methyl-1-hydroxyhexyl)phenoxymethyl]quinoline.

3. The compound according to claim 1 which is 2-[3-(1,2,2-trimethyl-1-hydroxyhexyl)phenoxymethyl]quinoline.

4. The compound according to claim 1 which is 2-[3-(6-[3-chlorophenoxy]-1-hydroxyhexyl)phenoxymethyl]quinoline.

5. The compound according to claim 1 which is 2-[3-(6-phenoxy-1-hydroxyhexyl)phenxoymethyl]quinoline.

6. The compound according to claim 1 which is 2-[3-(6-phenoxy-2,2-dimethyl-1-hydroxyhexyl)phenoxymethyl]quinoline.

7. The compound according to claim 1 which is 2-[3-(6-[3-trifluoromethylphenxoy]-1-hydroxyhexyl)-phenoxymethyl]quinoline.

8. The compound according to claim 1 which is 2-[3-(6-[3-chlorophenoxy]-1-methyl-1-hydroxyhexyl)-phenoxymethyl]quinoline.

9. The compound according to claim 1 which is 2-(3-(1-hydroxy-5,5,5-trifluoropentyl)phenoxymethyl)-quinoline.

10. The compound according to claim 1 which is 2-(3-(1-hydroxy-6,6,6-trifluorohexyl)phenoxymethyl)-quinoline.

11. The compound according to claim 1 which is 2-(3-(1-hydroxyheptyl)phenoxymethyl)quinoline.

12. The compound according to claim 1 which is 4-(3-(1-hydroxy-5,5,5-trifluoropentyl)phenoxymethyl)-quinoline.

13. The compound according to claim 1 which is 4-(3-(6-phenoxy-1-hydroxyhexyl)phenoxymethyl)-quinoline.

14. The compound according to claim 1 which is 2-(3-(1-hydroxy-1-methyl-5,5,5-trifluoropentyl)phenoxymethyl)quinoline.

15. The compound according to claim 1 which is 2-(3-(1-hydroxy-2,2-dimethyl-5,5,5-trifluoropentyl)-phenoxymethyl)quinoline.

16. The compound according to claim 1 which is 2-(3-(1,2,2-trimethyl-5,5,5-trifluoro-1-hydroxypentyl)-phenoxymethyl)quinoline.

17. The compound according to claim 1 which is 2-(3-(2,2-dimethyl-6,6,6-trifluoro-1-hydroxyhexyl)-phenoxymethyl)quinoline.

18. The compound according to claim 1 which is 2-(3-(1,2,2-trimethyl-6,6,6-trifluoro-1-hydroxyhexyl)-phenoxymethyl)quinoline.

19. The compound according to claim 1 which is 4-(3-(2,2-dimethyl-1-hydroxyhexyl)phenoxymethyl)-quinoline.

20. The compound according to claim 1 which is 2-(3-(1-acetoxyhexyl)phenoxymethyl)quinoline.

21. The compound according to claim 1 which is 2-(3-1-(1,1,1-trimethylacetoxy)hexyl)phenoxymethyl)-quinoline.

22. The compound according to claim 1 which is 2-(3-(1-acetoxy-5,5,5-trifluoropentyl)phenoxymethyl)-quinoline.

23. The compound according to claim 1 which is 2-(3-1-(1,1,1-(trimethylacetoxy)-5,5,5-trifluoropentyl)-phenoxymethyl)quinoline.

24. The compound according to claim 1 which is 2-(3-1-(1,1,1-(trimethylacetoxy)-6,6,6-trifluorohexyl)-phenoxymethyl)quinoline.

25. The compound according to claim 1 which is 2-(3-(2,2-dimethyl-1-(1,1,1-trimethylacetoxy)hexyl-phenoxymethyl)quinoline.

26. The compound according to claim 1 which is 2-(3-(2,2-dimethyl-6,6,6-trifluoro-1-(1,1,1-trimethylacetoxy)hexyl)phenoxymethyl)quinoline.

27. The compound according to claim 1 which is 3-(3-(1-hydroxyhexyl)phenoxymethyl)quinoline.

28. The compound according to claim 1 which is 6-(3-(1-hydroxyhexyl)phenoxymethyl)quinoline.

29. The compound according to claim 1 which is 2-(3-(1-hydroxyhexyl)benzyloxymethyl)quinoline.

30. The compound according to claim 1 which is 2-[3-(6-(3-trifluoromethylphenoxy)-1-hydroxhexyl)-phenoxymethyl]quinoline.

31. The compound according to claim 1 which is 2-[3-(6-phenoxy-1-hydroxy-1-methylhexyl)phenoxymethyl]quinoline.

32. The compound according to claim 1 which is 2-[3-(6-(3-trifluoromethylphenoxy)-1-hydroxy-1-methylhexyl)phenoxymethyl]quinoline.

33. 2-[3-(1-Hydroxyhexyl)phenoxymethyl]quinoline.

34. The compound according to claim 1 which is 2-(3-(6-phenoxy-1,2,2-trimethyl-1-hydroxyhexyl)-phenoxymethyl)quinoline.

35. The compound which is 2-[6-(1-hydroxyhexyl)-3-pyridyloxy]quinoline.

36. The compound according to claim 1 which is 2-(3-(6-benzyloxy-1-hydroxyhexyl)phenoxymethyl)-quinoline.

* * * * *

UNITED STATES PATENT AND TRADEMARK OFFICE
CERTIFICATE OF CORRECTION

PATENT NO. : 4,794,188

DATED : December 27, 1988

INVENTOR(S) : John Musser, et al.

It is certified that error appears in the above-identified patent and that said Letters Patent is hereby corrected as shown below:

Column 1, line 8: "1984, abandoned, which" should read as --1984 which--

Column 3, line 60: "coppound" should read as --compound--

Column 5, line 37: "therapeuticalyy" should read as --therapeutically--

Column 5, line 49: "aaccharin" should read as --saccharin--

Column 5, line 51: "doage" should read as --dosage--

Column 6, line 17: "examplc" should read as --example--

Column 8, line 56: "5-hydroyymethyl" should read as --5-hydroxymethyl--

Column 10, line 23: "eetone" should read as --ketone--

Column 13, line 53: "(1-N,N-dimethylaninohexyl)" should read as --(1-N,N-dimethyl-aminohexyl)--

Column 14, line 47: "chlorid" should read as --chloride--

Column 15, lines 14-15: "volatiless" should read as --volatiles--

UNITED STATES PATENT AND TRADEMARK OFFICE
CERTIFICATE OF CORRECTION

PATENT NO. : 4,794,188

DATED : December 27, 1988

INVENTOR(S) : John Musser, et al.

It is certified that error appears in the above-identified patent and that said Letters Patent is hereby corrected as shown below:

Column 20, line 39: "lqquid" should read as --liquid--

Column 24, line 29: "thrroughly" should read as --thoroughly--

Column 27, line 39, Claim 1: insert $R_3$ is H, $C_1$ to $C_6$ alkyl, phenyl or benzyl;" after phenyl or benzyl--

Signed and Sealed this

Twenty-first Day of May, 1991

Attest:

HARRY F. MANBECK, JR.

Attesting Officer

Commissioner of Patents and Trademarks